(12) United States Patent
Amano et al.

(10) Patent No.: US 8,512,742 B2
(45) Date of Patent: Aug. 20, 2013

(54) TRANSDERMAL PREPARATION

(75) Inventors: Satoshi Amano, Tsukuba (JP);
Tomohiro Shinoda, Tsukuba (JP);
Natsumi Kase, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 13/318,370

(22) PCT Filed: Apr. 30, 2010

(86) PCT No.: PCT/JP2010/057659
§ 371 (c)(1),
(2), (4) Date: Nov. 1, 2011

(87) PCT Pub. No.: WO2010/126124
PCT Pub. Date: Nov. 4, 2010

(65) Prior Publication Data
US 2012/0058175 A1    Mar. 8, 2012

(30) Foreign Application Priority Data
May 1, 2009   (JP) ................................. 2009-112234

(51) Int. Cl.
*A61K 9/70*  (2006.01)
(52) U.S. Cl.
USPC ............................. 424/443; 424/400; 424/401
(58) Field of Classification Search
CPC .......... A61K 9/70; A61K 47/10; A61Q 19/00
USPC .......................... 424/443, 400, 401; 514/1.1
See application file for complete search history.

(56) References Cited

U.S. PATENT DOCUMENTS

| | | | |
|---|---|---|---|
| 4,820,525 A * | 4/1989 | Leonard et al. ............... | 424/486 |
| 5,364,628 A | 11/1994 | Kissel et al. .................. | 424/448 |
| 5,593,686 A | 1/1997 | Kissel et al. .................. | 424/448 |
| 5,626,866 A | 5/1997 | Ebert et al. .................... | 424/447 |
| 5,827,529 A | 10/1998 | Ono et al. ..................... | 424/448 |
| 2002/0102290 A1 | 8/2002 | Hirano et al. ................. | 424/448 |
| 2002/0128345 A1 * | 9/2002 | Paul ............................. | 523/112 |
| 2004/0170673 A1 | 9/2004 | Koch et al. .................... | 424/449 |
| 2006/0240086 A1 * | 10/2006 | Tateishi et al. ............... | 424/449 |
| 2007/0166362 A1 * | 7/2007 | Sakuma et al. ............... | 424/449 |
| 2008/0292685 A1 | 11/2008 | Wang et al. ................... | 424/449 |
| 2009/0068252 A1 | 3/2009 | Amano et al. ................. | 424/448 |
| 2010/0098747 A1 | 4/2010 | Iwao et al. .................... | 424/449 |

FOREIGN PATENT DOCUMENTS

| | | |
|---|---|---|
| JP | 59-184120 | 10/1984 |
| JP | 61-501324 | 7/1986 |
| JP | 04-305523 | 10/1992 |
| JP | 09-509960 | 10/1997 |
| JP | 2003-313122 | 11/2003 |
| JP | 2007-099759 | 4/2007 |
| JP | 2007-284378 | 11/2007 |
| JP | 2008-247899 | 10/2008 |
| WO | WO 98/25592 | 6/1998 |
| WO | WO 2007/099966 | 7/2007 |
| WO | WO 2009/026133 A2 | 2/2009 |
| WO | WO 2009/026135 A2 | 2/2009 |

OTHER PUBLICATIONS

JP2004-002246 by Miyazaki et al., oublished Jan. 2004, machine translation.*
Extended European Search Report from EPO Application No. 10769822.7, dated Jun. 12, 2013.

* cited by examiner

*Primary Examiner* — Janet Epps-Smith
*Assistant Examiner* — Yanzhi Zhang
(74) *Attorney, Agent, or Firm* — Licata & Tyrrell P.C.

(57) ABSTRACT

Provided is a transdermal preparation, which is capable of long-term (1-day to 7-day) release of a basic drug from a preparation, continuously and at a consistent concentration; shows little reduction over time in the drug content, even if multiple drugs are contained in the preparation; and is produced by a simple process. The transdermal preparation comprises a substrate, and an adhesive layer containing a basic drug and a water-soluble polymer.

14 Claims, 2 Drawing Sheets

TRANSDERMAL PREPARATION

This patent application is a U.S. National Stage Application of International Application No. PCT/JP2010/057659, filed Apr. 30, 2010, which claims the benefit of priority from Japanese Application No. 2009-112234, filed May 1, 2009, teachings of each of which are herein incorporated by reference in their entirety.

TECHNICAL FIELD

The present invention relates to a transdermal preparation that continuously delivers a certain amount of a drug through the skin.

BACKGROUND ART

To obtain drug effects from a drug by its administration, an oral administration method is generally used; however, transdermal administration methods have many advantages over oral administration methods. For example, in an oral administration method, the drug absorbed in the bowel is, before it exhibits a drug effect in a desired site, first metabolized in the liver and most of its quantity is decomposed; whereas in a transdermal administration method, since the absorbed drug does not first pass through the liver during its body circulation, the drug effect is not significantly reduced by the metabolism in the liver. Moreover, transdermal administration methods have further advantages that drug effects are long lasting, and the methods have a certain type of drug-release characteristics.

Furthermore, as an advantage of transdermal administration methods, alleviation of side effects by maintaining a constant blood concentration of the drug through its sustained release is expected. In particular, there is a tendency that transdermal administration preparations that can be administered over a long period of time (1 day to 7 days) are preferred from the viewpoint of compliance of patients. To make such a long-term (1 day to 7 days) administration preparation, an effective amount of the drug must be absorbed transdermally during the administration period; accordingly, a large amount of the drug must be retained in the preparation. Considering the practicable area and thickness of preparations, it is necessary that the highest possible concentration (at least 10 mass % or more, preferably 20 mass % or more, and more preferably 30 mass % or more) of a drug is contained in a preparation. However, because many basic drugs are low soluble to rubber adhesives and silicone adhesives, it is very difficult to contain a basic drug with 10 mass % or more in these adhesives while maintaining properties of the adhesives. Meanwhile, to produce a transdermal administration preparation comprising a basic drug with the high concentration of 10 mass % or more, use of an acrylic adhesive having high polarity is advantageous in terms of solubility to drugs; however, many basic drugs react with acrylic acid alky ester or acrylic acid, i.e., a constitutional monomer of acrylic adhesives, possibly leading to a problem of a decrease in the drug content, etc.

Bisoprolol is a basic drug, which is a β blocker that selectively blocks $β_1$ receptors of the sympathetic nervous system, does not have an intrinsic sympathomimetic effect, and is a therapeutic drug of essential hypertension.

Currently, bisoprolol is used only in the form of oral preparation in clinical setting, and has relatively small effects on bronchial tubes due to its high selectivity for $β_1$. However, when bisoprolol is orally administered, it may possibly induce symptoms such as bradycardia, dizziness, and malaise; from the viewpoint of stability of blood concentration over long period of time and sustainability of effects, development of transdermal administration preparations such as adhesive patches has been desired, rather than oral administration.

Fluvoxamine is a basic drug as well, which is a selective serotonin reuptake inhibitor (SSRI) acting on the re-absorption of serotonin in the synapse, and is an antidepressant.

When SSRI such as fluvoxamine is orally administered to a patient, side effects such as nausea, diarrhea, and gastrointestinal tract disturbance are concerned, and defect of decreased compliance occurs such as withdrawal of taking the drug. Therefore, methods for administration other than oral administration are investigated in recent years.

Considering such a current situation, making a transdermal preparation comprising bisoprolol, in particular making an adhesive patch, has been proposed (Patent Literatures 1-4). For example, Patent Literature 4 discloses a transdermal preparation that can transdermally administer a drug stably for a long period of time, by laminating a skin adhesion layer onto a backing and a drug reservoir layer comprising bisoprolol. However, since an acrylic adhesive is used for the drug reservoir layer, the drug content tends to decrease during long period of storage.

Furthermore, Patent Literature 5 discloses an adhesive patch comprising a selective serotonin reuptake inhibition constituent as a pharmacologically-active component. However, in this literature, it is not that a basic drug is contained in a high concentration by means of comprising water-soluble polymer in the adhesive patch, and a means for achieving this is not provided as well.

Moreover, in Patent Literature 6, a transdermal therapeutic device having at least three layers consisting of a drug-non-penetrating backing layer, a drug reservoir layer comprising a serotonin receptor antagonist positioned between the backing layer and a drug-release layer, and the drug-release layer consisting of a pressure-sensitive adhesive layer that can control release of the drug. However, this literature neither enables to contain a basic drug in a high concentration, nor provides a means for achieving this.

CITATION LIST

Patent Literature

Patent Literature 1: JP A 2007-99759
Patent Literature 2: JP A 2003-313122
Patent Literature 3: JP A 2008-247899
Patent Literature 4: WO 2007/99966
Patent Literature 5: JP A 2007-284378
Patent Literature 6: WO 98/25592

SUMMARY OF INVENTION

Technical Problem

Under such circumstances, the present inventors have come to the recognition that transdermal preparations that can be administered stably for a long term while comprising a basic drug such as bisoprolol and fluvoxamine at high concentrations in the preparation, and that have excellent properties of the preparation and time-course stability of the drug (content stability), have to be produced. Namely, a problem to be solved by the present invention is to provide a transdermal preparation that can release a basic drug continuously at a constant concentration for a long term (1-7 days), and wherein its time-course decrease in the drug content is small although a large amount of the drug is contained in the preparation, and whose production process is simple.

Solution to Problem

The present inventors have investigated intensively so as to solve the above problem, and found that a transdermal preparation having a configuration in which an adhesive layer comprising a basic drug and a water-soluble polymer is on the backing-side makes it possible to contain the basic drug at high concentrations, and thus completed the present invention.

Namely, the present invention relates to a transdermal preparation having a backing and an adhesive layer, wherein the adhesive layer comprises a basic drug and a water-soluble polymer.

Furthermore, the present invention relates to said transdermal preparation in which the adhesive layer consists of multiple layers, wherein the adhesive layer comprises a drug reservoir layer and a skin adhesion layer, and said drug reservoir layer comprises 10-60 mass % of a basic drug and a water-soluble polymer.

In addition, the present invention relates to said transdermal preparation, wherein the basic drug is bisoprolol.

Furthermore, the present invention relates to said transdermal preparation, wherein the basic drug is fluvoxamine.

In addition, the present invention relates to said transdermal preparation, wherein the water-soluble polymer is one or more kinds selected from the group consisting of cellulose derivative, polyvinyl pyrrolidone, and aminoalkyl(meth)acrylate copolymer.

Furthermore, the present invention relates to said transdermal preparation, wherein the cellulose derivative is hydroxypropyl cellulose.

In addition, the present invention relates to said transdermal preparation, wherein the weight ratio of the drug to the water-soluble polymer in the drug reservoir layer is from 15:85 to 70:30.

Furthermore, the present invention relates to said transdermal preparation, wherein the skin adhesion layer comprises styrene-isoprene-styrene block copolymer.

In addition, the present invention relates to said transdermal preparation, wherein the skin adhesion layer further comprises one or more kinds selected from the group consisting of a synthetic rubber other than styrene-isoprene-styrene block copolymer, a tackifier resin, and a plasticizer.

Furthermore, the present invention relates to said transdermal preparation, wherein the synthetic rubber other than styrene-isoprene-styrene block copolymer is one or more kinds selected from the group consisting of polyisobutylene, isoprene rubber, styrene-butadiene-styrene copolymer, and styrene-butadiene rubber.

In addition, the present invention relates to said transdermal preparation, wherein the tackifier resin is one or more kinds selected from the group consisting of a rosin derivative, an alicyclic saturated hydrocarbon resin, an aliphatic hydrocarbon resin, a terpene resin, and a maleic acid resin.

Furthermore, the present invention relates to said transdermal preparation, wherein the plasticizer is one or more kinds selected from the group consisting of petroleum oil, squalane, squalene, vegetable oil, silicone oil, dibasic acid esters, liquid rubber, liquid fatty acid esters, diethylene glycol, polyethylene glycol, glycol salicylate, propylene glycol, dipropylene glycol, triacetin, triethyl citrate, and crotamiton.

In addition, the present invention relates to said transdermal preparation, wherein the adhesive layer further comprises one or more kinds selected from the group consisting of a solubilizer, a transdermal absorption enhancer, an antioxidant, a filler, a crosslinking agent, a preservative, and a UV absorber.

Furthermore, the present invention relates to said transdermal preparation, wherein the solubilizer and/or the absorption enhancer is one or more kinds selected from the group consisting of carbon chain number 6-20 of fatty acid, fatty alcohol, fatty acid ester, amide, ethers, aromatic organic acid, aromatic alcohol, aromatic organic acid ester and ether (that may be saturated or unsaturated, cyclic, linear or branched); as well as lactic acid esters, acetic acid esters, monoterpene compounds, sesquiterpene compounds, Azone, Azone derivatives, pirotiodecane, glycerin fatty acid esters, propylene glycol fatty acid esters, sorbitan fatty acid esters (Span), polysorbate (Tween), polyethylene glycol fatty acid esters, polyoxyethylene hardened castor oils, polyoxyethylene alkyl ethers, sucrose fatty acid esters, and vegetable oil.

In addition, the present invention relates to said transdermal preparation, wherein the ratio of the thickness of the drug reservoir layer to that of the skin adhesion layer is from 1:3 to 5:1.

Furthermore, the present invention relates to a method for producing said transdermal preparation by laminating the drug reservoir layer with the skin adhesion layer.

Advantageous Effects of Invention

Regarding the transdermal preparation of the present invention, its production process is simple, and the drug can be transdermally absorbed at a stable skin permeation rate continuously for a long period of time, and time-course stability of the drug is good, and its adhesion to the skin is good, with only a little irritation to the skin; accordingly, the transdermal preparation of the present invention is extremely effective to the treatment of a wide range of disorders.

DESCRIPTION OF EMBODIMENTS

Figure 1:
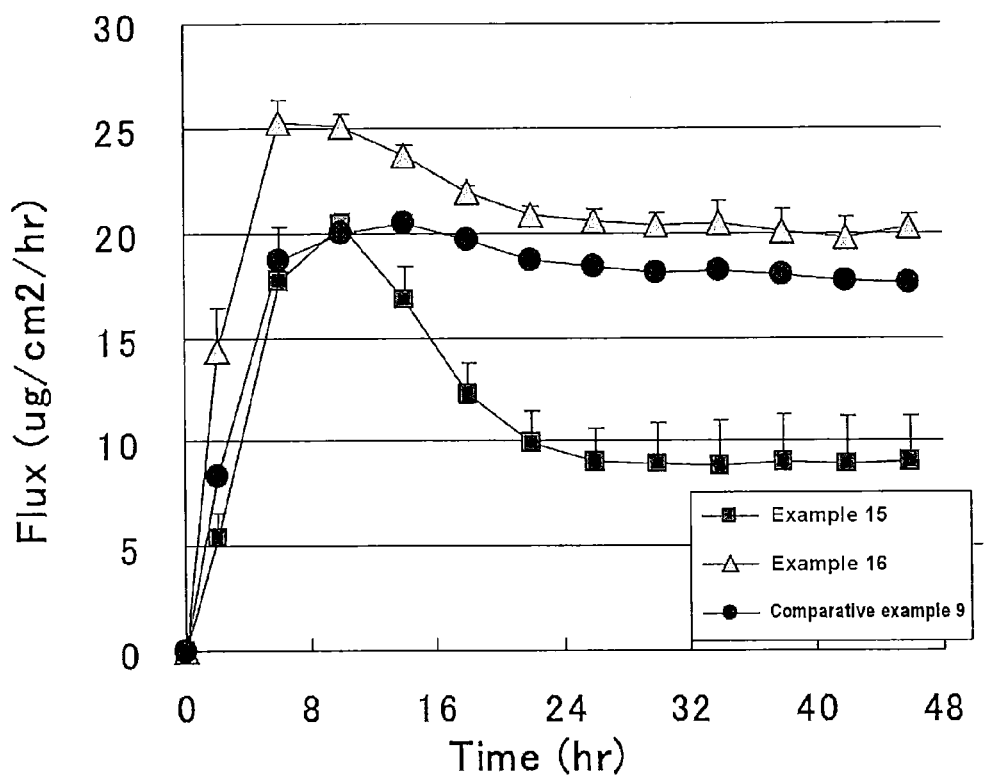
FIG. 1 is a graph showing results of the skin permeation test of hairless mice. (Test example 3)

The transdermal preparation of the present invention is an adhesive patch consisting of a backing and an adhesive layer, wherein the adhesive layer comprises a basic drug and a water-soluble polymer.

In addition, in the transdermal preparation of the present invention, the adhesive layer is divided into two or more, a plurality of, layers, and a skin adhesion layer is present as a layer for adhering to the skin which is located at most distant from the backing, and a drug reservoir layer is present between the backing and the skin adhesion layer; this configuration is preferred in terms of sustained release of drugs.

The backing of the transdermal preparation of the present invention is not particularly limited as long as it can retain the adhesive layer; any stretchable or non-stretchable backing may be used. Examples are not particularly limited, and may be selected from woven fabric, knitted fabric, non-woven fabric, polyurethane, polyester, polyvinyl acetate, polyvinylidene chloride, polyethylene, polyethylene terephthalate, aluminum sheet, etc., or a complex material thereof, or a laminate thereof.

In particular, stretchable or non-stretchable sheet made from polyethylene terephthalate is preferred.

The adhesive layer of the transdermal preparation of the present invention comprises a drug and a water-soluble polymer. The water-soluble polymer is not particularly limited, and examples include cellulose derivatives (hydroxypropyl cellulose, hydroxypropyl methyl cellulose, hydroxyethyl cellulose, carboxymethyl cellulose, methyl cellulose, etc.), polyvinyl pyrrolidone, polyvinyl alcohol, and aminoalkyl (meth)acrylate copolymer.

Among these, from the viewpoint of being able to retain a large amount (high concentration) of a basic drug such as bisoprolol and fluvoxamine, and being excellent in the stability of drug content, and excellent in the properties of the adhesive layer (good cohesion characteristics without bleeding and cold flow), hydroxypropyl cellulose, polyvinyl pyrrolidone, and aminoalkyl(meth)acrylate copolymer are preferably used.

The adhesive layer comprising such water-soluble polymer is able to comprise a basic drug such as bisoprolol and fluvoxamine at high concentrations in a stable manner, and exhibits good properties of adhesive layer.

The adhesive layer of the present invention preferably does not comprise water nor lower alkyl having a carbon number of 1-6, in order to ensure good properties (good cohesion characteristics without bleeding and cold flow).

The molecular weight (nominal viscosity) of the water-soluble polymer affects the properties such as cohesion and hardness of the adhesive layer. In particular, molecular weight of hydroxypropyl cellulose (display viscosity) is preferably 1.0 mPA·s-4000 mPA·s, more preferably 1.0 mPA·s-400 mPA·s.

The drug used in the transdermal preparation of the present invention is not particularly limited; specifically, examples include hypnotic (sleeping drug)/sedative agent, antipyretic/antiphlogistic analgesic, steroidal anti-inflammatory agent, stimulant/analeptic drug, psychoneurotic agent, hormone drug, local analgesic, agent for the urinary organs, muscle relaxant suxametonium, agent for the reproductive organs, antiepileptic drug, autonomic agent, antiparkinsonian agent, diuretic agent, respiratory stimulant, antimigraine agent, antihistaminic agent, bronchodilator, cardiotonic agent, coronary vasodilator, peripheral vasodilator, smoking-cessation aid, antihypertensive agent, agent for arrhythmia, anti-malignant ulcer agent, anti-hyperlipidemic drug, hypoglycemic agent, therapeutic agent for peptic ulcer, cholagogue, entrokinesis improving agent, agent for liver disorder, anti-allergic agent, anti-viral agent, antibiotic, agent for habitual intoxication, anorectic, chemotherapeutic agent, blood coagulant, anti-Alzheimer agent, serotonin receptor antagonistic antiemetic drug, therapeutic agent for gout, narcotic analgesic and others.

As the drug used in the transdermal preparation of the present invention, among the above drugs, antihypertensives (α-blocker, β-blocker, Ca antagonist, ACE inhibitor, angiotensin II receptor blocker) are preferable, and β-blocker is particularly preferable and, among others, bisoprolol, which achieves the effect of the present invention significantly, is the most preferable.

In addition, as the drug used in the transdermal preparation of the present invention, among the above drugs, psychoneurotic agents (antipsychotic, antidepressant, antimanic, anxiolytic) are preferable, and antidepressant is particularly preferable and, among others, selective serotonin reuptake inhibitors such as fluvoxamine, etc., which exhibit the effect of the present invention significantly, are the most preferable.

Furthermore, the drugs are used as a free base or a pharmacologically acceptable salt.

The pharmacologically acceptable salts are not particularly limited, and examples include hydrochloride, hydrobromate, nitrate, sulfate, phosphate, formate, acetate, trifluoroacetate, propionate, lactate, tartrate, oxalate, fumarate, maleate, citrate, malonate, methanesulfonate and the like.

The content of the drug mixed in the transdermal preparation of the present invention is, in order to achieve transdermal administration of the drug at a therapeutically effective amount through a long-term application period (1-7 days), generally, 10-60 mass %, preferably 20-50 mass %, more preferably 30-50 mass %, based on the total amount of the adhesive layer or drug reservoir layer.

The drug may be contained in the drug reservoir layer in a dissolved state, supersaturated crystalline state, or dispersed state.

When the content of the drug mixed in the transdermal preparation of the present invention is 10 mass % or less relative to the total amount of the adhesive layer or drug reservoir layer, it may not be preferable because sufficient skin permeability cannot be obtained through the administration period of the preparation; when the content is 60 mass % or more, sometimes sufficient cohesion as an adhesive patch cannot be maintained or stability of the content may be decreased. Since the transdermal preparation of the present invention comprises a water-soluble polymer, it can retain a large amount of basic drugs with high polarity such as bisoprolol and fluvoxamine, or pharmacologically acceptable salts thereof; and simultaneously, it exhibits a small degree of decrease in the content.

In the transdermal preparation of the present invention, the ratio of the content of the drug to that of the water-soluble polymer in the adhesive layer or drug reservoir layer is preferably from 15:85 to 70:30, more preferably from 25:75 to 55:45, and furthermore preferably from 35:65 to 55:45, from the viewpoint of ensuring time-course stability of the drug and properties of the adhesive layer (ensuring cohesion, prevention of bleeding and cold flow).

In the transdermal preparation of the present invention, it is preferable that the adhesive layer has a configuration of having a drug reservoir layer and a skin adhesion layer, wherein the drug reservoir layer comprises a basic drug and a water-soluble polymer, and the skin adhesion layer is laminated on the drug reservoir layer and is to be in contact with the skin. In addition, the transdermal preparation of the present invention may further be provided with multiple layers between the backing and the drug reservoir layer, or between the drug reservoir layer and the skin adhesion layer, as long as the object of the present invention can be accomplished.

Examples of the base agent of the skin adhesion layer are not particularly limited, and include, for example, rubber adhesives, silicone adhesives, and acrylic adhesives; preferably a rubber adhesive is contained as an adhesive constituent. As the rubber adhesive constituent, styrene-isoprene-styrene block copolymer is particularly preferably used.

In the present invention, while the water-soluble polymer used in the drug reservoir layer has a high polarity, since the rubber adhesive constituent consists of a monomer constituent that does not have such a functional group, it has a low polarity and significantly different physical and chemical properties. When bisoprolol or fluvoxamine is used as the drug in the present invention, by laminating the skin adhesion layer having a rubber adhesive constituent on the drug reservoir layer comprising a water-soluble polymer, delivery of bisoprolol or fluvoxamine, having high polarity, from the drug reservoir layer into the skin adhesion layer can be effectively controlled, so that long-term sustained and stable transdermal absorption of bisoprolol or fluvoxamine can be achieved.

The content of the styrene-isoprene-styrene block copolymer in the skin adhesion layer is preferably 5 to 30 mass %; this is because, when the content is 5 mass % or less, there is a tendency that sufficient permeability and cohesion as an adhesive patch cannot be maintained, whereas when the content is 30 mass % or more, sufficient adhesive force as an adhesive patch cannot be maintained The skin adhesion layer of the transdermal preparation of the present invention may further comprise synthetic rubbers in addition to the above-mentioned styrene-isoprene-styrene block copolymer, and as to the synthetic rubbers, without limitation, polyisobutylene, isoprene rubber, styrene-butadiene-styrene copolymer, styrene-butadiene rubber, polysiloxane, etc. can preferably be used. Each of these synthetic rubbers maybe used singly, or in a combination of two or more kinds. Among them, polyisobutylene is especially preferable, and it is more preferable that two or more polyisobutylenes having different molecular weights are used in combination. As to the content of the synthetic rubber other than styrene-isoprene-styrene block copolymer in the skin adhesion layer, 1-30 mass % is preferable, and 5-20 mass % is more preferable.

Furthermore, in case that styrene-isoprene-styrene block copolymer (SIS) and polyisobutylene (PIB) are used for the skin adhesion layer of the transdermal preparation of the present invention, the degree of adherence to the skin can be varied arbitrarily by varying the composition ratio thereof. For example, if the mix ratio of the styrene-isoprene-styrene block copolymer is increased, the adhesive force can be decreased, and, in contrast, if the mix ratio of the polyisobutylene is increased, the adhesive force can be increased. The preferable mix ratio of SIS to PIB in the skin adhesion layer for maintaining the adhesive force of being able to adhere for a long period, and for preventing the adhesive residue from remaining on the skin upon peeling off is SIS/PIB=70/30 to 40/60.

Furthermore, a tackifier resin is preferably contained in the skin adhesion layer of the present invention in case that the adhesive force is not sufficient to maintain the application for at least 12 hours and, as usable tackifier resins, examples are not particularly limited and include rosin derivatives (e.g., rosin, glycerin esters of rosin, hydrogenated rosin, glycerin esters of hydrogenated rosin, pentaerythritol esters of rosin, etc.), alicyclic saturated hydrocarbon resins (e.g., Arkon (registered trademark) P-100, Arakawa Chemical Industries, Ltd.), aliphatic hydrocarbon resins (e.g., Quintone (registered trademark) B170, Zeon Corporation), terpene resins (e.g., Clearon (registered trademark) P-125, Yasuhara Chemical, Co., Ltd.), maleic acid resins and the like. In particular, glycerin esters of hydrogenated rosin, alicyclic saturated hydrocarbon resins and terpene resins are preferable.

These tackifier resins may be used singly, or in a combination of two or more kinds. The amount of mixing is not particularly limited, whereas 10-60 mass % in the skin adhesion layer is preferable, 20-60 mass % is more preferable, and 30-50 mass % is particularly preferable.

In addition, a plasticizer may be contained in the skin adhesion layer of the transdermal preparation of the present invention. Plasticizers are not particularly limited, and examples include petroleum oils (e.g., paraffinic process oil, naphthenic process oil, aromatic process oil, etc.), squalane, squalene, vegetable oils (e.g., olive oil, camellia oil, castor oil, tall oil, peanut oil), silicone oil, dibasic acid esters (e.g., dibutylphthalate, dioctylphthalate, etc.), liquid rubber (e.g., polybutene, liquid isoprene rubber), liquid fatty acid esters (isopropyl myristate, hexyl laurate, diethyl sebacate, diisopropyl sebacate), diethylene glycol, polyethylene glycol, glycol salicylate, propylene glycol, dipropylene glycol, triacetin, triethyl citrate, crotamiton and the like. In particular, liquid paraffin, liquid polybutene, isopropyl myristate, diethyl sebacate and hexyl laurate are preferable.

These plasticizers maybe used singly, or in a combination of two or more kinds. The amount of mixing of these plasticizers is not particularly limited, whereas 5-50 mass % in the skin adhesion layer is preferable, 10-40 mass % is more preferable, and 20-30 mass % is particularly preferable.

In addition, in the present invention, if required, solubilizers, transdermal absorption enhancers, antioxidants, fillers, cross-linking agents, preservatives or UV absorbers and the like can be mixed in the drug reservoir layer and/or skin adhesion layer.

As the solubilizer, any compounds having a dissolving effect to drugs may be used. In addition, as the absorption enhancer, any compounds that have been conventionally confirmed to have an absorption enhancing effect at the skin may be used.

The solubilizers and/or absorption enhancers are not particularly limited, and include, for example, carbon chain number 6-20 of fatty acid, fatty alcohol, fatty acid ester, amide, or ethers, aromatic organic acid, aromatic alcohol, aromatic organic ester or ether (that may be saturated or unsaturated, cyclic, linear or branched), as well as lactic acid esters, acetic acid esters, monoterpene compounds, sesquiterpene compounds, Azone, Azone derivatives, pirotiodecane, glycerin fatty acid esters, propylene glycol fatty acid esters, sorbitan fatty acid esters (Span), polysorbate (Tween), polyethylene glycol fatty acid esters, polyoxyethylene hardened castor oils (HCO), polyoxyethylene alkyl ethers, sucrose fatty acid esters, and vegetable oils, etc.

Antioxidants are not particularly limited, and preferable examples include tocopherol and its ester derivatives, ascorbic acid, ascorbyl stearate, nordihydroguaiaretic acid, dibutyl hydroxy toluene (BHT), butyl hydroxy anisole; fillers are not particularly limited, and preferable examples include calcium carbonate, magnesium carbonate, silicate (e.g., aluminum silicate, magnesium silicate, bentonite, kaolin, etc.), silicic acid, barium sulfate, calcium sulfate, calcium zincate, zinc oxide, titanium oxide; crosslinking agents are not particularly limited, and desirable examples include thermosetting resins such as amino resin, phenol resin, epoxy resin, alkyd resin, unsaturated polyester and others, isocyanate compounds, block isocyanate compounds, organic crosslinking agents, and inorganic crosslinking agents such as metal or metal compound. Furthermore, preservatives are not particularly limited, and preferable examples include ethyl p-hydroxy benzoate, propyl p-hydroxy benzoate, and butyl p-hydroxy benzoate; UV absorbers are not particularly limited, and preferable examples include p-amino benzoic acid derivatives, anthranilic acid derivatives, salicylic acid derivatives, coumarin derivatives, amino-acid compounds, imidazoline derivatives, pyrimidine derivatives, and dioxane derivatives.

The amount of mixing of each of the above solubilizers, transdermal absorption enhancers, antioxidants, fillers, crosslinking agents, preservatives, and UV absorbers is not particularly limited, whereas the total amount of the solubilizer, transdermal absorption enhancer, antioxidant, filler, crosslinking agent, preservative and UV absorber is, based on the total amount of all constituents in the adhesive layer, or based on the total amount of all constituents contained in each of the drug reservoir layer and the skin adhesion layer calculated separately for each layer, preferably 0.01-20 mass %, more preferably 0.1-10 mass %, and particularly preferably 0.1-5 mass %.

In addition, the transdermal preparation of the present invention can be provided with additional layers between the backing and the drug reservoir layer, or between the drug reservoir layer and the skin adhesion layer, such as, without limitation, layers of acrylic adhesive, rubber adhesive, water-soluble polymer, and release controlling membrane.

The thickness of the drug reservoir layer is not limited as long as a sufficient amount is contained and retained so that the therapeutic amount of the drug can be administered over a predetermined period (1-7 days); the thickness is preferably 25-400 μm, and more preferably 50-300 μm.

The thickness of the skin adhesion layer is not particularly limited as long as the preparation can be securely adhered during the application period, and also the drug release rate can be controlled; the thickness is preferably 10-200 μm, and more preferably 20-150 μm.

The thickness of the entire adhesive layer combining the drug reservoir layer and the skin adhesion layer is not particularly limited; in terms of comfortable feeling in adhesion without unpleasant sensation, it is preferably 35-600 μm, and more preferably 70-450 μm.

Moreover, the ratio of the thickness of the drug reservoir layer to that of the skin adhesion layer can be determined arbitrarily considering the stability, drug release control and adhesion characteristic of the preparation; generally, the ratio is preferably in the range from 1:5 to 5:1, and more preferably from 1:3 to 5:1.

The adhesive layer of the adhesive preparation of the present invention may be provided with detachable sheet on the side in contact with the skin, which is opposite to the backing. The detachable sheet is not particularly limited, and examples include a film such as of polyesters such as polyethylene terephthalate, polyvinyl chloride and polyvinylidene chloride; and a laminated film of high-quality paper and polyolefin. These detachable sheets are preferably siliconized on the surface of the side in contact with the adhesive layer. Siliconization makes it possible for the detachable sheet to be easily detached from the adhesive layer at the time of use.

The process for producing the transdermal preparation of the present invention is not particularly limited; as one embodiment thereof, for example, it can be produced as follows: a water-soluble polymer and a drug are dissolved in a solvent such as water and ethanol, etc., and after applying the obtained solution onto a release film and drying, a backing is adhered to the drug reservoir layer; meanwhile, a solution of a styrene-isoprene-styrene block copolymer, a synthetic rubber, a tackifier resin, and a plasticizer dissolved in an organic solvent is coated onto a detachable sheet, and dried to make a skin adhesion layer; then the skin adhesion layer and the previously-obtained drug reservoir layer from which the release film is detached are laminated together to give a preparation.

By using the transdermal preparation of the present invention, basic drugs such as bisoprolol and fluvoxamine can be administered stably for a long period (1 day to 7 days). Namely, the transdermal preparations having a configuration of the exemplary embodiment of the present invention can maintain a high skin permeation rate (Flux value) with low variation over time after the start of adhering, and can maintain the blood concentration stably for a long time, so that it is excellent in terms of compliance in the treatment of hypertension and depression. In addition, the preparation can be produced by a simple production process in which, as mentioned above, two layers are formed separately by means of usual solvent coating method and then laminated together, and moreover, it has an excellent adhesive force and a low stimulation to the skin, and it does not peel off even for a long time after adhered without skin irritation, and a degree of time-course decrease in the drug content is small; accordingly, it is useful as a transdermal preparation.

EXAMPLES

In the following, the present invention is explained in more details by way of examples. The present invention, however, is not limited to these examples. Furthermore, "%" means "mass %" unless otherwise expressly stated.

Evaluation of Drug Reservoir Layer

TABLE 1

| | Ex. 1 | Ex. 2 | Ex. 3 | Ex. 4 | Ex. 5 | Ex. 6 | Ex. 7 |
|---|---|---|---|---|---|---|---|
| Polyvinyl pyrrolidone (low molecular weight) | 60% | 55% | 50% | — | — | — | — |
| Polyvinyl pyrrolidone (high molecular weight) | — | — | — | 60% | 55% | 50% | — |
| Hydroxypropyl cellulose | — | — | — | — | — | — | 60% |
| Eudragit (R) EPO | — | — | — | — | — | — | — |
| Acrylic adhesive (—COOH group-containing type) | — | — | — | — | — | — | — |
| Bisoprolol | 40% | 45% | 50% | 40% | 45% | 50% | 40% |

| | Ex. 8 | Ex. 9 | Ex. 10 | Ex. 11 | Ex. 12 | Comp. Ex. 1 | Comp. Ex. 2 | Comp. Ex. 3 |
|---|---|---|---|---|---|---|---|---|
| Polyvinyl pyrrolidone (low molecular weight) | — | — | — | — | — | — | — | — |

TABLE 1-continued

| | | | | | | | | |
|---|---|---|---|---|---|---|---|---|
| Polyvinyl pyrrolidone (high molecular weight) | — | — | — | — | — | — | — | — |
| Hydroxypropyl cellulose | 55% | 50% | — | — | — | — | — | — |
| Eudragit (R) EPO | — | — | 60% | 55% | 50% | — | — | — |
| Acrylic adhesive (—COOH group-containing type) | — | — | — | — | — | 60% | 55% | 50% |
| Bisoprolol | 45% | 50% | 40% | 45% | 50% | 40% | 45% | 50% |

| | Ex. 13 | Ex. 14 | Comp. Ex. 4 | Comp. Ex. 5 |
|---|---|---|---|---|
| Hydroxypropyl cellulose | 80% | 85% | — | — |
| Acrylic adhesive (—OH group-containing type) | — | — | 80% | 85% |
| Fluvoxamine | 20% | 15% | 20% | 15% |

Examples 1-14

In accordance with the mix ratio listed in the above table of formulation, ethanol was added and dissolved into each polymer, and bisoprolol or fluvoxamine was added and stirred sufficiently to give a coating solution. Then, the obtained coating solution was coated on a polyethylene terephthalate release film, the ethanol as the solvent was removed by drying, to form an adhesive layer. After obtaining a predetermined thickness (200 μm), the adhesive layer was laminated with a polyethylene terephthalate backing, giving a transdermal preparation (Examples 1-14) of the present invention.

Comparative Examples 1-5

To an acrylic adhesive solution (—COOH group-containing type or —OH group-containing type, solvent: ethyl acetate/toluene), bisoprolol or fluvoxamine was added and stirred well to give a coating solution. Then, the obtained coating solution was coated on a polyethylene terephthalate release film, ethyl acetate and toluene as the solvents were removed by drying, to form an adhesive layer. After obtaining a predetermined thickness (200 μm), the adhesive layer was laminated with a polyethylene terephthalate backing, giving transdermal preparations of Comparative Examples 1-5.

TABLE 2

| | Comp. Ex. 6 | Comp. Ex. 7 | Comp. Ex. 8 |
|---|---|---|---|
| Styrene-isoprene-styrene block copolymer | 19.0% | 13.5% | — |
| Polyisobutylene (low molecular weight) | 5.5% | 9.5% | 73.0% |
| Polyisobutylene (high molecular weight) | 2.5% | 4.0% | 12.0% |
| Alicyclic saturated hydrocarbon resin | 41.0% | 41.0% | — |
| Liquid paraffin | 22.0% | 22.0% | 5.0% |
| Bisoprolol | 10.0% | 10.0% | 10.0% |

Comparative Examples 6-8

According to the mix ratio shown in the above table of formulation, styrene-isoprene-styrene block copolymer, polyisobutylene (high molecular weight), polyisobutylene (low molecular weight), alicyclic saturated hydrocarbon resin, and liquid paraffin were dissolved in toluene, then bisoprolol was added and stirred well to give a coating solution. Then, the obtained coating solution was coated on a polyethylene terephthalate release film, the solvent was removed by drying, to form an adhesive layer. After obtaining a predetermined thickness (100 μm), the adhesive layer was laminated with a polyethylene terephthalate backing, giving transdermal preparations of Comparative Examples 6-8.

Test Example 1

Stability Test of Drug Content

The transdermal preparations produced in Examples 1, 4, 7, 10, and 13, and Comparative Examples 1 and 4 were cut into a 10 cm$^2$ size, to give samples used for the test. Each sample was stored in a thermo-hygrostat chamber at the temperature of 60° C. and humidity of 75% for either 2 weeks or 1 month, then the contents of bisoprolol or fluvoxamine ($N_i$) were measured; these values and the contents of bisoprolol or fluvoxamine in the initial sample measurement ($N_0$) were substituted in the following relational equation (1) to obtain values of ($R_i$), which were assigned as the after-storage percentage (%) of bisoprolol or fluvoxamine relative to the initial value in each sample under each condition.

$$R_i(\%) = N_i/N_0 \times 100 \qquad (1)$$

(Extraction Method)

An adhesive layer, tetrahydrofuran (10 mL) was introduced in a centrifugation tube, and shaken for 1 hr. An internal standard substance (4-amino isopropyl benzoate/methanol solution) was added, then the volume was adjusted to 50 mL by adding methanol, and shaken for additional 1 hr. Then, the content of bisoprolol or fluvoxamine in each test sample was quantified by high-performance liquid chromatography.

TABLE 3

Drug-content stability

|  |  | Initial value | 60° C. 2 weeks | 1 month |
|---|---|---|---|---|
| Ex. 1 Polyvinyl pyrrolidone (low-molecular weight) Bisoprolol | Mean Relative to the initial value | 103.5 100.0 | 103.2 99.7 | 102.4 98.9 |
| Ex. 4 Polyvinyl pyrrolidone (high-molecular weight) Bisoprolol | Mean Relative to the initial value | 106.3 100.0 | 105.7 99.4 | 105.2 99.0 |
| Ex. 7 Hydroxypropyl cellulose Bisoprolol | Mean Relative to the initial value | 102.5 100.0 | 102.2 99.7 | 101.7 99.2 |
| Ex. 10 Eudragit (RT) EPO Bisoprolol | Mean Relative to the initial value | 103.4 100.0 | 102.8 99.4 | 101.7 98.4 |
| Comp. Ex. 1 Acrylic adhesive (—COOH group-containing type) Bisoprolol | Mean Relative to the initial value | 101.6 100.0 | 99.1 97.5 | 96.5 95.0 |
| Ex. 13 Hydroxypropyl cellulose Fluvoxamine | Mean Relative to the initial value | 82.7 100.0 | 56.0 67.7 | — — |
| Comp. Ex. 4 Acrylic adhesive (—OH group-containing type) Fluvoxamine | Mean Relative to the initial value | 55.8 100.0 | 18.4 33.0 | — — |

As shown in Table 3, a large decrease in the drug content over time is observed in the adhesive layer having an acrylic adhesive as the base agent (Comparative Examples 1 and 4); in contrast, the adhesive layer having a water-soluble polymer as the base agent (Examples 1, 4, 7, 10 and 13) has excellent stability of drug content.

Test Example 2

Physical Property Evaluation

Physical properties of the transdermal preparations comprising the bisoprolol-containing adhesive layer in Examples 1, 4, 5, 7, 8 and 10 and Comparative Examples 1, 2, 6, 7 and 8 were evaluated in terms of strength of cohesion and presence/absence of bleeding.

TABLE 4

Evaluation of physical properties

|  | Cohesion | Bleeding |
|---|---|---|
| Ex. 1 | Δ | ○ |
| Ex. 4 | ○ | ○ |
| Ex. 5 | ○ | ○ |
| Ex. 7 | ○ | ○ |
| Ex. 8 | ○ | ○ |
| Ex. 10 | X | ○ |
| Comp. Ex. 1 | ○ | ○ |
| Comp. Ex. 2 | ○ | ○ |
| Comp. Ex. 6 | X | X |
| Comp. Ex. 7 | X | X |
| Comp. Ex. 8 | X | X |

Cohesion
○: No thread-like adhesive, no oozing
Δ: Oozing at 60° C., but not at normal temperature
X: Thread-like adhesive and oozing at normal temperature
Bleeding
○: No bleeding
X: Bleeding From the results of Table 4, bleeding of a drug occurred and cohesion decreased with the transdermal preparations comprising the adhesive layer having a rubber adhesive as the base agent (Comparative Examples 6-8); therefore, a high concentration of a drug could not be contained. In contrast, the transdermal preparations having the adhesive layer comprising an acrylic adhesive as the base agent (Comparative Examples 1 and 2) showed good properties. In addition, the transdermal preparations having the adhesive layer comprising a water-soluble polymer, i.e., polyvinyl pyrrolidone (Examples 1, 4 and 5) or hydroxypropyl cellulose (Examples 7 and 8) showed strong cohesion without bleeding, and good properties.

Results of the test example 1 showed that the drug reservoir layer comprising a water-soluble polymer and a drug has better stability of drug content compared to the drug reservoir layer of the comparative examples, and results of the test example 2 showed that hydroxypropyl cellulose and polyvinyl pyrrolidone exhibit good properties such as cohesion and bleeding.

Evaluation of Transdermal Preparations

Examples 15 and 16, Comparative Example 9

Formulation of Skin Adhesion Layer

TABLE 5

| Styrene-isoprene-styrene block copolymer | 18% |
|---|---|
| Polyisobutylene (high molecular weight) | 6% |
| Polyisobutylene (low molecular weight) | 12% |
| Alicyclic saturated hydrocarbon resin | 42% |
| Liquid paraffin | 22% |

In accordance with the mix ratio shown in the above formulation, styrene-isoprene-styrene block copolymer, polyisobutylene (high molecular weight), polyisobutylene (low molecular weight), alicyclic saturated hydrocarbon resin and liquid paraffin were dissolved in toluene to give a coating solution, which was coated on a polyethylene terephthalate release film, and the solvent was removed by drying to form a skin adhesion layer of the transdermal preparation of the present invention having a predetermined plaster thickness (50 μm).

Then, the adhesive layers obtained in Examples 4 and 7 and in Comparative Example 1 as the drug reservoir layer were joined to the skin adhesion layer, giving the transdermal preparations of Examples 15 and 16, and Comparative Example 9.

Test Example 3

Skin Permeation Test of Hairless Mice

To the stratum corneum side of the skin (side of the body) extracted from a hairless mouse of 7-10 weeks old, the transdermal preparation (3 cm$^2$) obtained in Examples 15, 16 or Comparative Example 9 was adhered, and the sample was mounted on a flow-through-type diffusion cell with its dermis side positioned at the receptor-layer side. Phosphate buffered saline of pH 7.4 was circulated on the receptor layer side such that the temperature at the skin surface became 32±1° C. Under the condition of the flow rate of the receptor liquid: 4 mL/hr and sampling: every 4 hr, bisoprolol concentration was measured by high-performance liquid chromatography.

FIG. 1 shows the permeation rate per 1 hr for Examples 15, 16 and Comparative Example 9, obtained from the measurements of the flow rate and bisoprolol concentration.

As shown in FIG. 1, the skin permeation rate for Example 15 (polyvinylpyrrolidone)transiently pyrrolidone) transiently increased, then decreased, indicating that sufficient skin permeation rates cannot be maintained; whereas in Example 16 (hydroxypropyl cellulose), same as in Comparative Example 9 (acrylic adhesive), a sufficient skin permeation rate is exhibited, and moreover, the skin permeation rate can be continuously maintained.

Test Example 4

Skin Permeation Test of Humans

By using a human skin (abdomen) for testing having a thickness of approximately 500 μm from the stratum corneum, the transdermal preparation obtained in Example 16 or Comparative Example 9 was adhered, which was mounted on a flow-through-type diffusion cell with the dermis side positioned at the receptor-layer side. Phosphate buffered saline of pH 7.4 was circulated on the receptor layer side such that the temperature at the skin surface became 32±1° C. Under the condition of the flow rate of the receptor liquid: 4 mL/hr and sampling: every 4 hr, bisoprolol concentration was measured by high-performance liquid chromatography.

Figure 2:
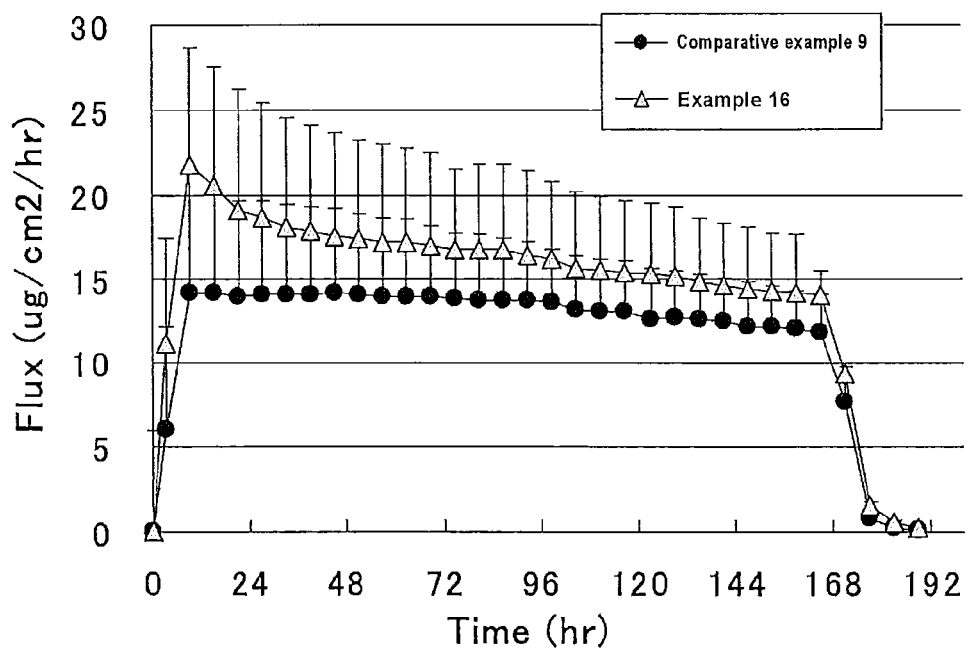
FIG. 2 is a graph showing results of the skin permeation test of human skins. (Test example 4)

As shown in FIG. 2, the preparation of Example 16 exhibited skin permeation sustainability for 1 week, similarly to the preparation of Comparative Example 9.

As described above, the transdermal preparation of the present invention shows only a slight decrease in the drug content with time even when a high concentration of a basic drug is contained in the drug reservoir layer, and has good cohesion, without causing bleeding and cold flow, and also has excellent properties. Furthermore, it can realize transdermal absorption of a drug continuously for 1 week with a stable rate; therefore, the inventive preparation is extremely useful for the treatment of disorders for which bisoprolol and fluvoxamine are effective therapeutic agents.

The invention claimed is:

1. A transdermal preparation having a backing and an adhesive layer for delivering a selected amount of bisoprolol through the skin continuously for a period of 1 to 7 day(s), wherein the adhesive layer comprises multiple layers, said multiple layers comprising a drug reservoir layer and a skin adhesion layer;

wherein said drug reservoir layer comprises bisoprolol at 30-50 mass % based on the total amount of the drug reservoir layer and a water-soluble polymer;

wherein the weight ratio of bisoprolol to the water-soluble polymer in the drug reservoir layer is from 35:65 to 55:45; and wherein the skin adhesion layer comprises styrene-isoprene-styrene block copolymer.

2. The transdermal preparation according to claim 1 wherein the water-soluble polymer is one or more kind selected from the group consisting of cellulose derivative, polyvinyl pyrrolidone, and aminoalkyl (meth)acrylate copolymer.

3. The transdermal preparation according to claim 2, wherein the water-soluble polymer is hydroxypropyl cellulose.

4. The transdermal preparation according to claim 1, wherein the skin adhesion layer comprises styrene-isoprene-styrene block copolymer.

5. The transdermal preparation according to claim 1, wherein the skin adhesion layer further consists of a synthetic rubber other than styrene-isoprene-styrene block copolymer, a tackifier resin, and a plasticizer.

6. The transdermal preparation according to claim 5, wherein the synthethic rubber other than styrene- isoprene-styrene block copolymer is selected from the group consisting of polyisobutylene, isoprene rubber, styrene-butadiene-styrene copolymer, and styrene-butadiene rubber.

7. The transdermal preparation according to claim 5, wherein the tackifier resin is one or more kinds selected from the group consisting of a rosin derivate, an alicyclic saturated hydrocarbon resin, an aliphatic hydrocarbon resin, a terpene resin, and a maleic acid resin.

8. The transdermal preparation according to claim 5, wherein the plasticizer is one or more kinds selected from the group consisting of petroleum oil, squalane, squalene, vegetable oil, silicone oil, dibasic acid esters, liquid rubber, liquid fatty acid esters, diethylene glycol, polyethylene glycol, glycol salicylate, propylene glycol, dipropylene glycol, triacetin, triethyl citrate, and crotamiton.

9. The transdermal preparation according to claim 1, wherein the adhesive layer further comprises one or more kinds selected from the group consisting of a solubilizer, a transdermal absorption enhancer, an antioxidant, a filler, a crosslinking agent, a preservative, and a UV absorber.

10. The transdermal preparation according to claim 9, wherein the solubilizer and/or the absorption enhancer is one or more kinds selected from the group consisting of carbon chain number 6-20 of fatty acid, fatty alcohol, fatty acid ester, amide, ethers, aromatic organic acid, aromatic alcohol, aromatic organic acid ester and ether (that may be saturated or unsaturated, cyclic, linear or branched); as well as lactic acid esters, acetic acid esters, monoterpene compounds, sesquiterpene compounds, Azone, Azone derivatives, pirotiodecane, glycerin fatty acid esters, propylene glycol fatty acid esters, sorbitan fatty acid esters (Span), polysorbate (Tween), polyethylene glycol fatty acid esters, polyoxyethylene hardened castor oils, polyoxyethylene alkyl ethers, sucrose fatty acid esters, and vegetable oil.

11. The transdermal preparation according to claim 2, wherein the ratio of the thickness of the drug reservoir layer to that of the skin adhesion layer is from 1:3 to 5:1.

12. The transdermal preparation according to claim 1, wherein the basic drug is a free base of bisoprolol.

13. A method for producing the transdermal patch according to claim 1 by laminating the drug reservoir layer with the skin adhesion layer.

14. A method for delivering a certain amount of a drug through the skin continuously for a period of 1 to 7 day(s) by applying the transdermal preparation according to claim 1 to the skin.

* * * * *

UNITED STATES PATENT AND TRADEMARK OFFICE
CERTIFICATE OF CORRECTION

PATENT NO. : 8,512,742 B2  
APPLICATION NO. : 13/318370  
DATED : August 20, 2013  
INVENTOR(S) : Amano et al.

Page 1 of 2

It is certified that error appears in the above-identified patent and that said Letters Patent is hereby corrected as shown below:

On the Title Page,  
Item (75) delete "Tsukuba" where it appears three times  
Item (75) insert --Ibaraki-- three times where "Tsukuba" appeared In the Claims  
Column 15, line 66, delete "30-50"  
Column 15, line 66, add --30-60--

Column 16, lines 15-17, delete "4. The transdermal preparation according to claim 1, wherein the skin adhesion layer comprises styrene-isoprene-styrene block copolymer."

Column 16, line 18, delete "5."  
Column 16, line 18, add --4.--

Column 16, line 22, delete "6."  
Column 16, line 22, add --5.--  
Column 16, line 22, delete "claim 5,"  
Column 16, line 22, add --claim 4,--

Column 16, line 27, delete "7."  
Column 16, line 27, add --6.--  
Column 16, line 27, delete "claim 5,"  
Column 16, line 27, add --claim 4,--

Column 16, line 29, delete "derivate,"  
Column 16, line 29, add --derivative--

Column 16, line 32, delete "8."  
Column 16, line 32, add --7.--

Signed and Sealed this  
Twenty-fourth Day of December, 2013

Margaret A. Focarino  
*Commissioner for Patents of the United States Patent and Trademark Office*

CERTIFICATE OF CORRECTION (continued)
U.S. Pat. No. 8,512,742 B2

Column 16, line 32, delete "claim 5,"
Column 16, line 32, add --claim 4,--

Column 16, line 40, delete "9."
Column 16, line 40, add --8.--

Column 16, line 45, delete "10."
Column 16, line 45, insert --9.--
Column 16, line 45, delete "claim 9,"
Column 16, line 45, insert --claim 8,--

Column 16, line 60, delete "11."
Column 16, line 60, insert --10.--
Column 16, line 60, delete "claim 2,"
Column 16, line 60, insert --claim 1,--

Column 16, line 63, delete "12."
Column 16, line 63, insert --11.--

Column 16, line 65, delete "13."
Column 16, line 65, insert --12.--

Column 17, line 1, delete "14."
Column 17, line 1, insert --13.--